(12) United States Patent
Piomelli

(10) Patent No.: US 6,974,568 B2
(45) Date of Patent: Dec. 13, 2005

(54) TREATMENT FOR COUGH

(75) Inventor: Daniele Piomelli, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 298 days.

(21) Appl. No.: 09/864,920

(22) Filed: May 23, 2001

(65) Prior Publication Data

US 2002/0035150 A1 Mar. 21, 2002

Related U.S. Application Data

(60) Provisional application No. 60/206,591, filed on May 23, 2000.

(51) Int. Cl.[7] ................................................. A61L 9/04

(52) U.S. Cl. ..................... 424/45; 514/654; 514/665; 514/666

(58) Field of Search ................................. 514/654, 665, 514/666; 424/45

(56) References Cited

U.S. PATENT DOCUMENTS

| | | | |
|---|---|---|---|
| 4,464,378 A | 8/1984 | Hussain |
| 5,596,106 A | 1/1997 | Cullinan et al. |
| 5,618,955 A | 4/1997 | Mechoulam et al. |
| 5,631,297 A | 5/1997 | Pate et al. |
| 5,635,530 A | 6/1997 | Mechoulam et al. |
| 5,747,524 A | 5/1998 | Cullinan et al. |
| 5,925,672 A | 7/1999 | Piomelli et al. |
| 5,977,180 A | 11/1999 | Pate et al. |
| 5,990,170 A | 11/1999 | Della Valle et al. |
| 6,013,648 A | 1/2000 | Rinaldi et al. |
| 6,017,919 A | 1/2000 | Inaba et al. |
| 6,028,084 A | 2/2000 | Barth et al. |
| 6,359,010 B1 | 3/2002 | Geracioti, Jr. et al. |

FOREIGN PATENT DOCUMENTS

| | | |
|---|---|---|
| EP | 0 570 920 A1 | 11/1993 |
| WO | WO 94/12466 A1 | 6/1994 |
| WO | WO 99/60987 A2 | 12/1999 |
| WO | WO 99/64389 A1 | 12/1999 |

OTHER PUBLICATIONS

Stengel et al. Pulmonary actions of anandamide, an endogenous cannabinoid receptor agonist in guinea pigs, European Jouna of Pharmacology, vol. 355 (1998) pp. 57–66.*
British Medical Association: Therapeutic Uses of Cannabis, Amsterdam harwood acadmeic publishers 1997, excerpt provided.*
Seltzman, H., "Structure and receptor activity for classical cannabinoids" Curr Med Chem. 6(8):685–704 (1999).
Shamsuddin et al., Database Medline on STN, Accession No. 1998082798, "Regulation of leukotriene and platelet–activating factor synthesis in human alveolar macrophages", *J. Lab. and Clin. Med.*, Dec. 1997, vol. 130, No. 6, pp. 615–626.
Stengel et al., "Pulmonary actions of anandamide, an endogenous cannabinoid receptor agonist, in guinia pigs," *European Journal of Pharmacology*, Jan. 1998, vol. 355, pp. 57–66.

(Continued)

Primary Examiner—Frederick Krass
Assistant Examiner—Amy Lewis
(74) Attorney, Agent, or Firm—Townsend and Townsend and Crew LLP

(57) ABSTRACT

The invention discloses the existence of cannabinoid receptors in the airways, which are functionally linked to inhibition of cough. Locally acting cannabinoid agents can be administered to the airways of a subject to ameliorate cough, without causing the psychoactive effects characteristic of systemically administered cannabinoids. In addition, locally or systemically administered cannabinoid inactivation inhibitors can also be used to ameliorate cough. The present invention also defines conditions under which cannabinoid agents can be administered to produce anti-tussive effects devoid of bronchial constriction.

28 Claims, 12 Drawing Sheets

Formula I     Formula II     Formula III

OTHER PUBLICATIONS

Zhu et al., "Cytosolic Phospholipase A2 Activation is Essential for beta 1 and beta 2 Integrin–Dependent Adhesion of Human Eosinophils," *Journal of Immunology*, Jul. 1999, vol. 163, No. 6, pp. 3423–3429.

Sugiura et al., "2–Archidonoylglycerol and the cannabinoid receptors," *Chemistry and Physics Lipids*, Jun. 2000, vol. 108, No. 1–2, pp. 89–106.

De Petrocellis et al., "Endocannabinoids and fatty acid amides in cancer, inflammation and related disorders," *Chemistry and Physics of Lipids*, 108 (2000) pp. 191–209.

Gordon et al., "Antitussive Activity of Some Naturally Occurring Cannabinoids in Anesthetized Cats," *European Journal of Pharmacology*, 35 (1976) pp. 309–313.

Zou, G., "Endogenous cannabinoid system," *Life Sciences*, vol. 9, No. 5, pp. 197–199, Oct. 1997, Shanghai Institute of Materia Medica, Chinese Academy of Sciences, Shanghai 200031.

* cited by examiner

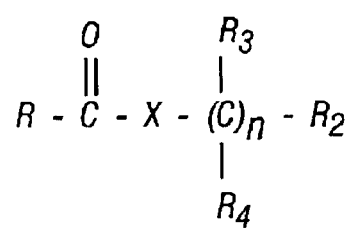 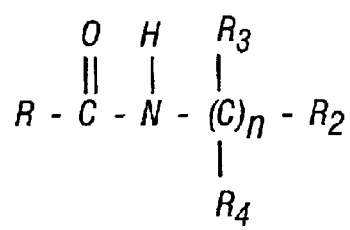 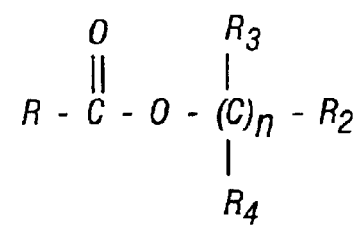
Formula I   Formula II   Formula III
FIG. 1A
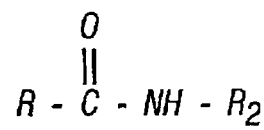 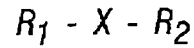
Formula IV   Formula V
FIG. 1B   FIG. 1C

TREATMENT FOR COUGH

RELATED APPLICATIONS

This application claims the benefit of priority under 35 U.S.C. §119(e) to U.S. Provisional Application No. 60/206,591, filed May 23, 2000. The aforementioned application is explicitly incorporated herein by reference in its entirety and for all purposes.

STATEMENT AS TO FEDERALLY SPONSORED RESEARCH

This invention was made with Government support under a grant from the National Institutes of Health. The Government may have certain rights in this invention.

TECHNICAL FIELD

This invention relates to pharmaceutical compositions for preventing the initiation of cough and methods for using the compositions for the treatment of cough. More particularly, the invention relates to the local administration of a therapeutically effective amount of a pharmaceutical composition comprising at least one direct or indirect cannabinoid receptor agonist to produce an anti-tussive effect without significant delivery of the agonist(s) to the systemic circulation.

BACKGROUND

Administration of the main active constituent of the cannabis plant, $\Delta^9$-tetrahydrocannabinol ($\Delta^9$-THC), produces in animals and humans alleviation of cough and bronchospasm, which suggest a possible application of cannabis-like (cannabinoid) compounds for the treatment of cough. The potential therapeutic value of this observation is hindered, however, by two factors. First, the systemic administration of cannabinoid compounds produces significant psychoactive effects (for example, memory impairment, dysphoria, alteration in the perception of time, and habit formation). Second, some asthmatic patients who receive $\Delta^9$-THC respond to this compound with a paradoxical bronchial constriction. Therefore, there exists a need for compounds, or pharmaceutical preparations thereof, which can prevent or alleviate cough in animals and humans without producing significant psychoactive effects.

SUMMARY OF THE INVENTION

In one general aspect, the present invention discloses the existence of cannabinoid receptors in the airways, which are functionally linked to inhibition of cough. Further, the invention teaches that local administration of locally acting cannabinoid agents in the airways reduce cough, without causing the psychoactive effects characteristic of systemically administered cannabinoids. Even further, the present invention defines conditions under which cannabinoid agents can be administered to produce anti-tussive effects devoid of bronchial constriction. Specifically, the invention demonstrates that cannabinoid compounds produce bronchial constriction when the intrinsic constricting tone of the vagus nerve is reduced or eliminated.

In another aspect, the present invention also teaches the local or systemic use of cannabinoid inactivation inhibitors, alone or in conjunction with a cannabinoid receptor agonist, to ameliorate cough.

The pharmaceutical compositions and methods of the present invention are characterized by their ability to inhibit cough initiation and/or signaling from the upper airways to the central nervous system. Specifically, the present invention results in the peripheral inhibition of cough signaling. Without being bound by any theory, it is believed that the pharmaceutical compositions of the present invention short-circuit the intracellular signaling cascade initiating cough by activating CB1 cannabinoid receptors found in the upper airways of mammals. The present invention regulates cough signaling at the periphery by the activation of local CB1 cannabinoid receptors where it is believed that endogenous cannabinoids participate in filtering emerging cough signals within the upper airways. The present invention unexpectedly achieves the above superior desired anti-tussive effects without the dysphoric side effects and habit-forming properties characteristic of centrally acting cannabimimetic or opiate drugs.

The invention provides a method for ameliorating or preventing cough in a subject, wherein the method comprises administration to the subject of a cannabinoid receptor agonist having anti-tussive properties without any significant psychoactive effects. The subject may be animal or human. As an example, one method of treating cough in a mammal may comprise topically administering into the upper airways (for example, by aerosol) an effective amount of at least one locally acting cannabinoid receptor agonist in a pharmaceutically acceptable excipient for topical administration.

In the methods of the invention, a cannabinoid receptor agonist, or a pharmaceutical composition thereof, in accordance to the present invention can include cannabinoid receptor agonists having the general formula I:

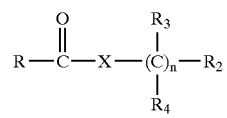

wherein X is N—R1 or O;

R is a saturated or unsaturated, chiral or achiral, cyclic or acyclic, substituted or unsubstituted hydrocarbyl group with 11 to 29 carbon atoms, optionally incorporating up to 6 oxygen or sulfur atoms;

R1, R3 and R4 are selected independently from hydrogen, alkyl (C1–4), alkenyl (C2–4), alkynyl (C2–4), cycloalkyl (C3–6), or hydroxyalkyl group with from 2 to 4 carbon atoms;

R2 is OH or O—CO-alkyl, where the alkyl group has from 1 to 4 carbon atoms; and n is selected from 2 to 4.

When R2 is OH and X is N—H, they may be combined through the carbonyl group to form a heterocyclic ring structure, e.g an oxazolidinone ring. Alternatively, when R2 is OH and X is N—H, they may be combined to form a heterocyclic ring structure, e.g. a morpholine ring.

In particular, the invention contemplates a family of amides with the generic structure shown below and active as cannabinoid receptor agonists having formula II:

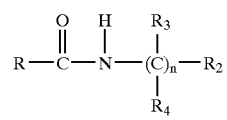

wherein R is a saturated or unsaturated, substituted or unsubstituted hydrocarbyl group with from 15 to 29 carbon atoms, optionally incorporating up to 3 oxygen or sulfur atoms;

R3 and R4 are selected independently from hydrogen, alkyl (C1–4), alkenyl (C2–4), alkynyl (C2–4), cycloalkyl (C3–6), or hydroxyalkyl group with from 2 to 4 carbon atoms;

R2 is OH or O—CO-alkyl, where the alkyl group has from 1 to 4 carbon atoms; and n is selected from 2 to 4.

When R2 is OH and X is N—H, they may be combined to form a heterocyclic ring structure.

The present invention also contemplates a family of esters with the generic structure shown below and active as cannabinoid receptor agonists having formula III:

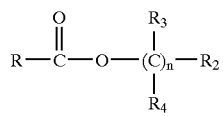

wherein R is a saturated or unsaturated, substituted or unsubstituted hydrocarbyl group with from 15 to 29 carbon atoms, optionally incorporating up to 3 oxygen atoms;

R3 and R4 are selected independently from hydrogen, alkyl (C1–4), alkenyl (C2–4), alkynyl (C2–4), cycloalkyl (C3–6), or hydroxyalkyl group with from 2 to 4 carbon atoms;

R2 is OH or O—CO-alkyl, where the alkyl group has from 1 to 4 carbon atoms; and n is selected from 2 to 4.

The invention further contemplates a family of amides with the generic structure shown below and active as inhibitors of endogenous cannabinoid inactivation in accordance with the present invention having formula IV:

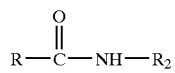

wherein R is a polyunsaturated, substituted or unsubstituted hydrocarbyl group with from 18 to 22 carbon atoms;

R2 is selected independently from substituted or unsubstituted cycloalkyl (C3–6) group and substituted or unsubstituted phenyl group (e.g., p-hydroxyphenyl, p-hydroxy-o-methyl-phenyl).

The invention also contemplates a family of fatty acid derivatives with the generic structure shown below and active as inhibitors of endogenous cannabinoid inactivation having formula V:

wherein R1 is a saturated or polyunsaturated, substituted or unsubstituted hydrocarbyl group with from 6 to 22 carbon atoms;

X is —C=O or $SO_2$—; and

R2 is a halogen or a halogen-substituted methyl group.

In accordance with another aspect of the present invention, there are disclosed pharmaceutical compositions for treating cough comprising the following examples of direct and indirect acting cannabinoid receptor agonists: arachidonylethanolamide (anandamide), (R)-(+) arachidonyl-1¹-hydroxy-2¹-propylamide, cis-7,10,13,16-docosatetraenoylethanolamide, homo-delta-linoleyethanolamide, N-propyl-arachidonylethanolamide, N-ethyl-arachidonylethanolamide, and 2-arachidonylglycerol. There are also disclosed pharmaceutical compositions for treating cough comprising the following examples of cannabinoid inactivation inhibitors: N-(4-hydroxyphenyl)-arachidonylamide, palmitylsulphonylfluoride, and arachidonyltrifluoromethylketone.

The cannabinoid receptor agonist and/or cannabinoid inactivation inhibitors, and pharmaceutically acceptable excipient, may, among other things, be formulated as an aerosol, spray, or solution, to be inhaled, to be administered orally, or to be administered parenterally, such as intravenously.

The locally acting cannabinoid receptor agonist and/or cannabinoid inactivation inhibitor, and pharmaceutically acceptable excipient, may be administered in conjunction with at least one additional therapeutic agent from the group consisting of anti-inflammatory compounds, systemic antitussives, and local anesthetics.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits cited herein are expressly incorporated by reference for all purposes.

DESCRIPTION OF THE DRAWINGS

FIGS. 1A–C depict chemical structures of cannabinoid compounds and inhibitors of endogenous cannabinoid inactivation.

FIG. 1A shows the general chemical structure of the direct-acting cannabinoid compounds of the present invention.

FIG. 1B shows the general chemical structure of a representative cannabinoid inactivation inhibitor (inhibitor of anandamide transport).

FIG. 1C shows the general chemical structure of another representative cannabinoid inactivation inhibitor (inhibitor of anandamide hydrolysis).

FIG. 2A is a bar graph showing the constricting effect of capsaicin (Caps, mg per kg, intravenous, i.v.) on guinea pig bronchial smooth muscle and its antagonism by the vanilloid receptor antagonist capsazepine (Cpz, 0.2 mg per kg, i.v.).

FIG. 2B is a bar graph showing the dose-dependent inhibitory effects of anandamide (AEA, mg per kg, i.v.) on capsaicin (30 mg per kg)-evoked bronchospasm in the absence or presence of the CB1 antagonist SR141716A (SR1, 0.5 mg per kg, i.v.) or the CB2 antagonist SR144528 (SR2, 0.3 mg per kg, i.v.).

FIG. 2C is a bar graph summarizing data showing the inhibitory effects of anandamide on capsaicin-evoked cough in the absence or presence of SR141716A (0.5 mg per kg, i.v.) or SR144528 (0.3 mg per kg, i.v.).

FIG. 3A is a bar graph summarizing the dose-dependent effect of anandamide (AEA, mg per kg, i.v.) on bronchial smooth muscle, in the presence or absence of the CB1 antagonist SR141716A (SR1, 0.2 mg per kg, i.v.) (n=6 for each condition).

FIG. 3B is a bar graph summarizing the dose-dependent effects of anandamide (5–30 mg per animal, intratracheal) in the absence or presence of SR141716A (SR1, 0.3 mg per kg, i.v.) (n=6 for each condition). SR141716A was administered 15 min before anandamide.

FIG. 3C is a representative tracing illustrating the effect of anandamide (100 µM) on isotonic muscle tension in guinea pig parenchyma strips and its reversal by the CB1 antagonist SR141716A (1 µM).

FIG. 3D is a response of the same lung strip of FIG. 3C to histamine (His, 10 µM) shown for comparison. The upward deflections are caused by repeated washes of the lung strip.

FIG. 3E is a bar graph summarizing the dose-dependent contractions of lung parenchyma in the presence of anandamide (µM) and antagonism of this effect by SR141716A (1 µM) (n=6 for each condition).

FIGS. 4A–B show silver-intensified gold particles labeling CB1 cannabinoid receptors, indicated by thin arrows, on serial sections of axon terminals in a bronchiole. Axon terminals containing small electron-translucent and large dense-core vesicles (thick arrow) are embedded in the collagen matrix and are surrounded by bronchial smooth muscle cells (BSM).

FIG. 4C shows that, in some cases, cannabinoid receptor labeling was observed in proximity of vesicle clusters (arrowhead), indicating putative neurotransmitter release sites.

FIGS. 4D–E show serial sections in the adventitious layer reveal multiple axon terminals packed together into glial capsules.

FIGS. 4F–G show co-localization of cannabinoid receptor and neuropeptide Y (NPY) immunoreactivities. Immunogold labeling of CB1 receptors is visible on the membrane of axon terminals, labeled a1 and a2, filled with electron-dense NPY immunoreactivity. N indicates the nucleus of a putative Schwann cell. Scale bars: 0.2 µm (scales for FIGS. 4B and 4E are the same as in FIGS. 4A and 4D, respectively).

FIG. 5A is a bar graph summarizing the bronchoconstricting effects of capsaicin (mg per animal, intratracheal) in the absence or presence of the CB1 antagonist SR141716A (0.2 mg per kg, i.v.).

FIG. 5B is a bar graph summarizing the tussigenic effects of capsaicin (0.3 µM, 4 min aerosol) in the absence or presence of SR141716A (0.2 mg per kg, i.v.).

FIGS. 6A–B are representative high-performance liquid chromatography/mass spectrometry tracings for selected ions characteristic of endogenous anandamide (mass-to-charge ratio m/z=370, an adduct with $Na^+$, $[M+Na^+]$) and synthetic $[^2H_4]$anandamide (m/z=374, $[M+Na^+]$), which was added to the samples as an internal standard, respectively.

FIG. 6C is a bar graph summarizing the effects of EGTA (1 mM) or $Ca^{2+}$ (3 mM) on anandamide biosynthesis in rat lung membranes. $Ca^{2+}$ significantly stimulated anandamide formation (mean±s.e.m., *P<0.05, n=4).

FIGS. 7A–B show the chemical structures of alk-1-palmitoenyl-2-arachidonyl-sn-glycero-phosphoethanolamine-N-arachidonyl (NAPE 1) and alk-1-stearyl-2-arachidonyl-sn-glycero-phosphoethanolamine-N-arachidonyl (NAPE 2), respectively, two putative anandamide precursors.

FIGS. 7C–D are representative high-performance liquid chromatography/mass spectrometry tracings for selected ions characteristic of NAPE 1 (m/z=1009, deprotonated molecular ion, $[M-H]^-$) and NAPE 2 (m/z=1039, $[M-H]^-$), respectively.

FIGS. 7E–F are bar graphs summarizing that biosynthesis of NAPE 1 and NAPE 2, respectively, was significantly stimulated by incubation with $Ca^{2+}$ (3 mM) (mean±s.e.m., *P<0.05, n=4) as compared to EGTA. NAPE 2 was eluted from the column as a doublet and the areas under both peaks were combined for quantification.

Like reference symbols in the various drawings indicate like elements.

DETAILED DESCRIPTION

Figure 2B:
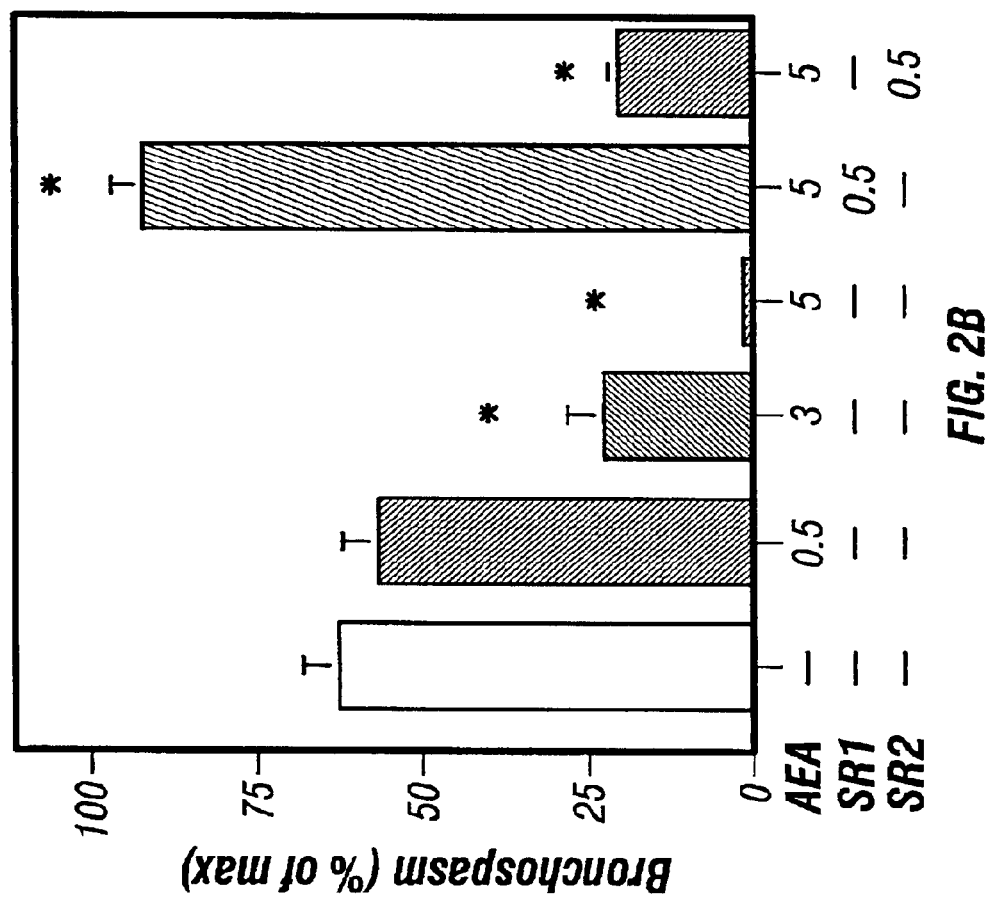
FIGS. 2A–C depict bar graphs summarizing data showing that anandamide inhibits capsaicin-evoked bronchospasm and cough in guinea pigs by activating peripheral CB1-type cannabinoid receptors. Results are expressed as mean±s.e.m, with n=3 for each condition. Asterisk indicates P<0.01.

The invention provides methods for ameliorating cough by means of (1) local administration of anandamide and other cannabinoid compounds, such as those illustrated by formulae I, II, and III; and/or (2) local or systemic administration of agents that increase the levels of endogenous or exogenously added cannabinoids in the upper respiratory tract by inhibiting cannabinoid inactivation, such as those represented by formulae IV and V.

Definitions

Unless defined otherwise, all technical and scientific terms used herein have the meaning commonly understood by a person skilled in the art to which this invention belongs. As used herein, the following terms have the meanings ascribed to them unless specified otherwise.

The phrase "administration of a pharmaceutical composition" incorporates the phrases common usage and refers to any appropriate means to give a pharmaceutical to a patient, taking into consideration the properties of the pharmaceutical composition and the preferred site of administration; e.g., in one embodiment, the pharmaceutical composition of the invention is inhaled into the lungs.

The term "ameliorating" as used herein refers to any indicia of success in the treatment or amelioration of an injury, pathology, condition, or symptom associated with a cough, including any objective or subjective parameter such as abatement; diminishing of symptoms or making the symptom, injury, pathology or condition more tolerable to the patient; decreasing the frequency or duration of the symptom or condition; improving a patient's physical or mental well-being; and preventing the onset of the symptom or condition of coughing. The treatment or amelioration of symptoms can be based on any objective or subjective parameter; including, e.g., the results of a patient's observations, physical examination, or, simply an improvement in the patient's sense of well-being.

The term "anandamide" as used herein refers to arachidonylethanolamides (see, e.g., U.S. Pat. No. 5,631,297) an endogenous lipid that activates cannabinoid receptors and mimics the pharmacological effects of $\Delta^9$-tetrahydrocannabinol, the active principle of hashish and marijuana. Anandamide analogs (equivalents) are described, e.g., in U.S. Pat. No. 5,977,180; WO 99/60987; WO 99/64389. See also, e.g., U.S. Pat. Nos. 6,028,084; 6,013,648; 5,990,170; 5,925,672; 5,747,524; 5,596,106; EP 0 570 920, WO 94-12466.

Compounds for use according to the invention, include but are not limited to, compounds of Formula Ib:

Formula Ib

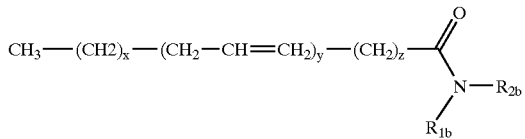

wherein $R_{1b}$ and $R_{2b}$ are each H or $(CH_2)_p$—$(R_{4b}CH)_q$—$(CH_2)_r$—$R_{3b}$, wherein p, q and r are each an integer of from 0 to 10, preferably 1 to 4; and $R_{3b}$ is OH, SH, $CH_3$, $CH=CH_2$, $C\equiv CH$, $C\equiv N$, F, Cl, Br or I, preferably OH, SH or F, more preferably OH; $R_{4b}$ is H or $(CH_2)_s CH_3$, wherein s is an integer from 0 to 10, preferably 0 to 4; provided that p+q+r+s is less than or equal to 10, preferably less than or equal to 4, preferably one of $R_{1a}$ and $R_{2b}$ is H and the other of $R_{1a}$ and $R_{2b}$ is $(CH_2)_p(R_{4b}CH)_q(CH_2)_r R_{3b}$;

x is an integer of from 0 to 18, preferably 2 to 5;

y is an integer of from 0 to 8, preferably 2 to 4; and z is an integer of from 0 to 18, preferably 2 to 5.

Non-limiting examples of the compounds represented by Formula (Ib) which can be employed in the present invention include the following:

arachidonylethanolamide
arachidonylethanethiolamide
arachidonylfluoroethylamide
7,10,13,16-docosatetraenylethanolamide
arachidanyipropanolamide
8,11,14-eicosatrienylethanolamide
Palmatidylethanolamide,
4,7,10,13,16,19-Docosahexaenylethanolamide
Arachidylfluoroethylamide
Arachidonylamide
Arachidonyl-1-methyl-ethanolamide
Arachidonyl-2-methyl-ethanolamide,
Gamma-linolenylethanolamide,
Linoleylethanolamide The term "locally acting cannabinoid" as used herein refers to cannabinoids of the general formulae I, II, or III. These cannabinoid analogs (equivalents) are described, e.g., in U.S. Pat. Nos. 5,635,530 and 5,618,955.

The term "direct cannabinoid receptor agonist" as used herein refers to a compound that binds to and activates CB1-type cannabinoid receptors.

The terms "indirect cannabinoid receptor agonist," "inhibitor of cannabinoid inactivation," or "cannabinoid inactivation inhibitor" as used herein refer to a compound that blocks the inactivating transport and/or degradation of cannabinoid compounds, consequently causing the accumulation of the cannabinoid substances at its sites of action.

The term "endogenous cannabinoid" as used herein refers to an endogenous agonist, or an equivalent thereof, of a cannabinoid receptor. Cannabinoid receptors are described, e.g., in U.S. Pat. No. 6,013,648. Endogenous agonists include, e.g., 2-arachidonylglycerol or anandamide. See also U.S. Pat. Nos. 6,028,084; 6,017,919; 596,106; 5,990,170; and, Seltzman (1999) Curr. Med. Chem. 6:685–704.

The term "cough" as used herein refers to the act of coughing or to the psychological or physiological sensations associated with causing a cough that can be ameliorated by administration of a pharmaceutical composition able to serve as a cannabinoid receptor agonist, to inhibit the inactivating transport (e.g., the intracellular transport), and/or to inhibit anandamide hydrolysis of endogenous, or exogenously added, cannabinoid substances. The term "cough" is broadly defined and not limited to a particular disease or cause creating this condition.

While the invention is not limited by any particular mechanism of action, in one embodiment, the invention contemplates administration of the locally acting cannabinoid receptor agonists and/or administration of cannabinoid inactivation inhibitors, which inhibit the inactivating transport of cannabinoid substances, and/or inhibit the anandamide hydrolysis of cannabinoid substances, as described in further detail, below.

The phrase "inhibiting cannabinoid inactivation" means any measurable amount of increase in the amount of extracellular free cannabinoid substance. While the invention is not limited by any specific mechanism, the inhibition of inactivation can be accomplished by the pharmaceutical composition by inhibition of inactivating uptake of the cannabinoid substance by the cell membrane or inhibition of anandamide hydrolysis.

The term "pharmaceutically acceptable excipient" incorporates the common usage and includes any suitable pharmaceutical excipient, including, e.g., water, saline, phosphate buffered saline, Hank's solution, Ringer's solution, dextrose/saline, glucose, lactose, or sucrose solutions, magnesium stearate, sodium stearate, glycerol monostearate, glycerol, propylene glycol, ethanol, and the like.

The terms "pharmaceutically effective" and "therapeutically effective" refer to a sufficient level of cough suppression or prevention in a human or animal resulting from the stimulation of cannabinoid or cannabinoid-like receptors. The term "therapeutically effective amount" and grammatical variations thereof refer to quantities of the active compound that are sufficient to produce the desired therapeutic effect when delivered topically (e.g., by aerosol) or systemically (e.g., orally).

General Methods

The methods of the invention use compounds capable of ameliorating cough by providing locally acting cannabinoids, inhibiting the inactivating transport of cannabinoids, and/or inhibiting anandamide hydrolysis. A variety of exemplary compounds useful in these methods are described herein. Exemplary routine methods for identifying these compounds are described herein. Exemplary routine methods for identifying inhibiting the inactivating transport of cannabinoids can be found in patent application U.S. Ser. No. 09/612,326, filed Jul. 6, 2000, the entirety of which is incorporated herein by reference.

The skilled artisan will recognize that compounds useful in the methods of the invention (e.g., arachidonylethanolamide) can be synthesized using a variety of procedures and methodologies, which are well described in the scientific and patent literature., e.g., Organic Syntheses Collective Volumes, Gilman et al. (Eds) John Wiley & Sons, Inc., NY; Venuti (1989) Pharm Res. 6:867–873. The invention can be practiced in conjunction with any method or protocol known in the art, which are well described in the scientific and patent literature. Therefore, only a few general techniques will be described prior to discussing specific methodologies and examples relative to the methods of the invention.

Structural Guidelines and Screening Tests to Design Locally Acting Cannabinoids Useful in the Methods of the Invention In the methods of the invention, pharmaceutical compositions comprising compounds capable of ameliorating cough are administered. These compounds act by locally activating cannabinoid receptors. An exemplary locally acting compound is an anandamide.

The biological actions of anandamide (arachidonylethanolamide), an endogenous cannabinoid lipid, in cough and bronchospasm inhibition is thought to be through the anandamide's activation of the CB1 receptors. Such actions are theorized by studies described herein using CB1 and CB2 receptor antagonists in the presence of locally acting cannabinoids. The experiments are described in greater detail below.

Furthermore, as described herein, the methods of the invention have been demonstrated to ameliorate cough by using art-accepted animal models. Specifically, the cannabinoids and their anti-tussive effects have been looked at in guinea pigs, rats, and cats, (Gordon, R. et al (1976) *Eur. J. Pharmacol. Vol.* 35 (2):309–313). In summary, these exemplary techniques and guidelines provide clear parameters to select for compounds useful as pharmaceutical compositions in the methods of the invention.

Figure 2A:
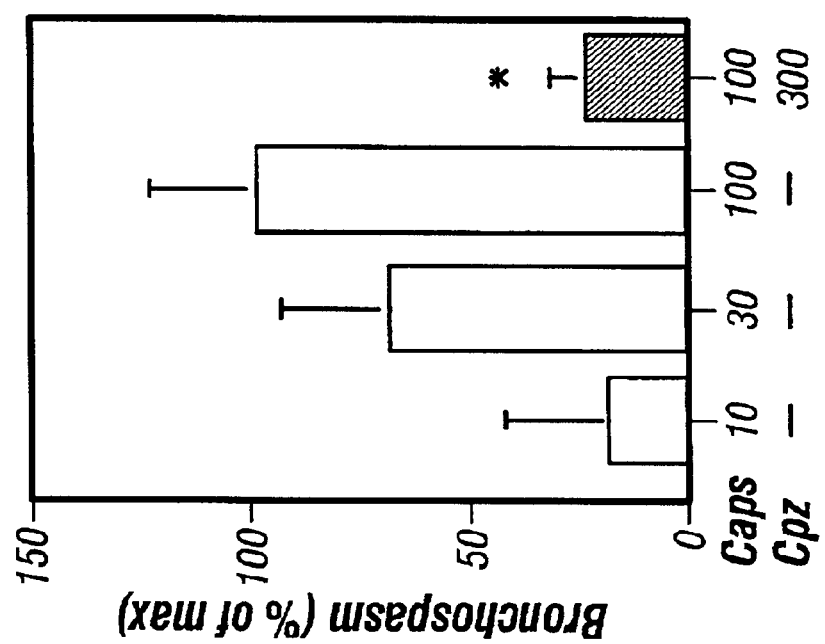
Figure 2C:
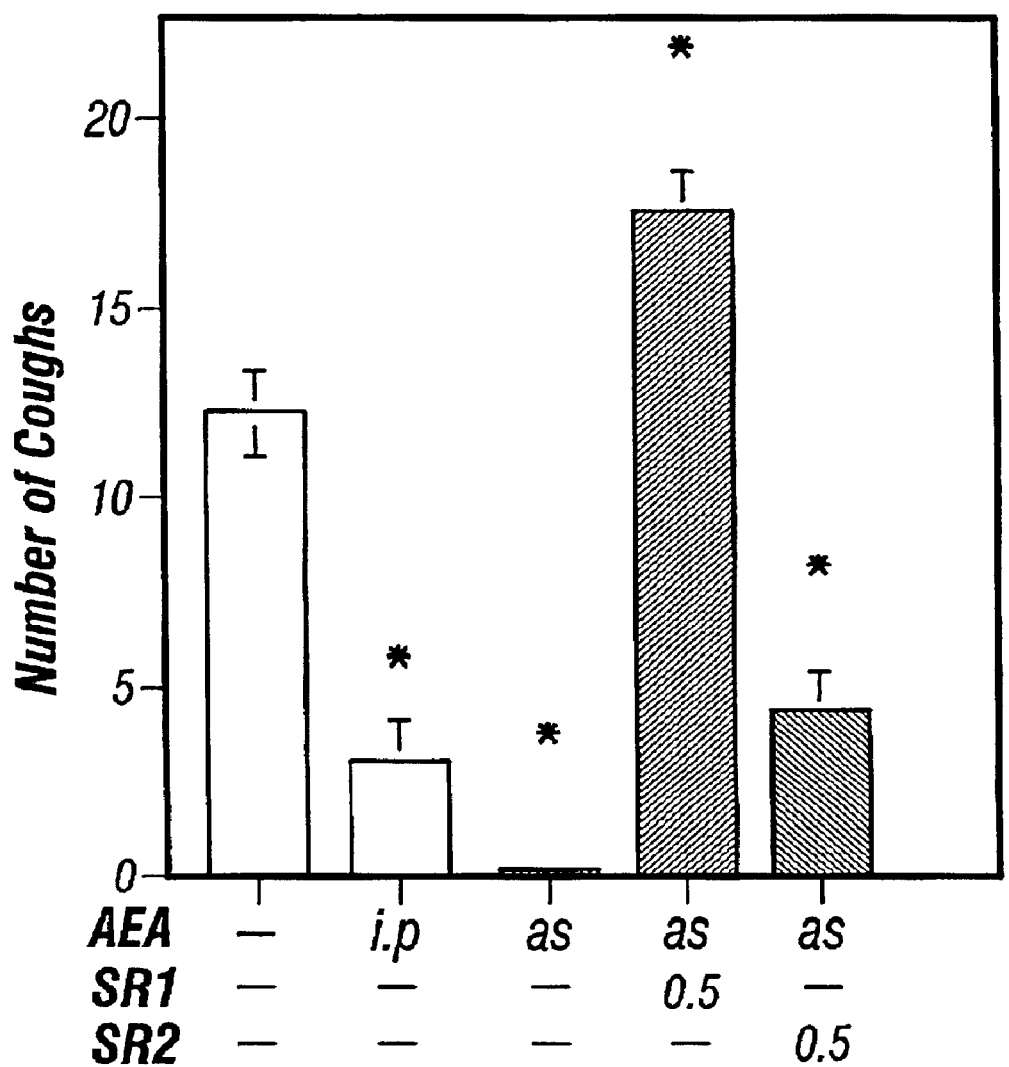

Cannabinoids, such as anandamide, which can be found endogenously, produces a profound inhibition of cough and bronchial smooth muscle contraction, when administered either systemically or by local application in the airways. FIGS. 2A–C show bar graphs of the level of bronchospasm and cough in guinea-pigs after administration of capsaicin, the pungent principle of chili pepper. Similar data were obtained in rats (intratracheal administration: 10 mg per animal, 41±6% of maximal bronchospasm; 30 mg per animal, 55±12%; 100 mg per animal, 81±19%; mean±s.e.m., n=3). This response was abrogated by anandamide when the compound was administered systemically before capsaicin in guinea pigs (FIG. 2B). Similar results were obtained in rats (capsaicin, 10 mg per animal, intratracheal administration: 37.2±4.2% of maximal bronchospasm; capsaicin after anandamide, 1 mg per kg, i.v., 14±7%; n=3). This effect was completely reversed by the selective CB1 cannabinoid antagonist SR141716A, but only slightly reduced with a maximal dose of the CB2 antagonist SR144528. Palmitylethanolamide, a structural analog of anandamide that inhibits nociception in mice but does not interact with CB1 cannabinoid receptors as described in Calignano et al. (1998) *Nature* 394, 277–281, was ineffective at alleviating capsaicin-evoked bronchospasm. When given as an aerosol to conscious guinea pigs, capsaicin stimulates C-fibre activity in the upper respiratory tract and triggers cough. Systemic anandamide reduced capsaicin-evoked cough, an effect that was abrogated by CB1 cannabinoid receptor blockade, as shown in FIG. 2C. Importantly, aerosolized anandamide also produced potent anti-tussive effects (FIG. 2C), which were not accompanied by any visual signs of cannabinoid intoxication.

Figure 3B:
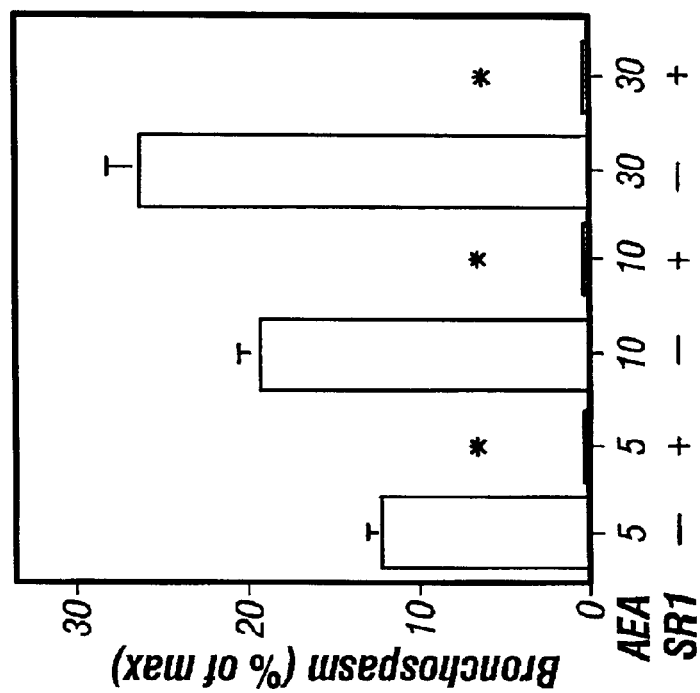
FIGS. 3A–E depict bar graphs and representative tracings of muscle tension showing that anandamide causes bronchoconstriction in vagotomized, atropine-treated guinea pigs by activating peripheral CB1 cannabinoid receptors. Asterisk indicates P<0.01.
Figure 3A:
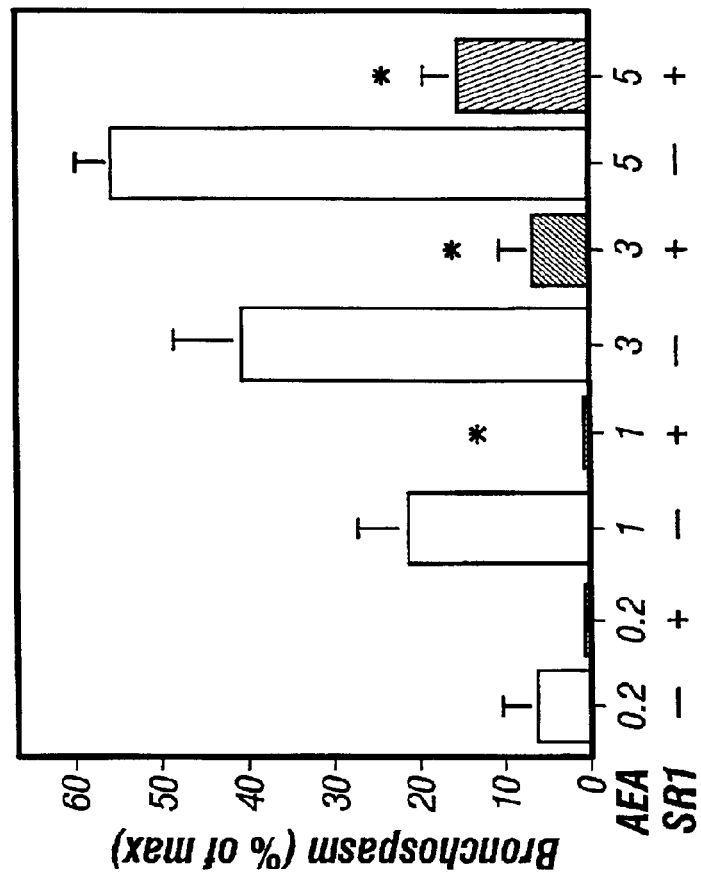
Figure 3C:
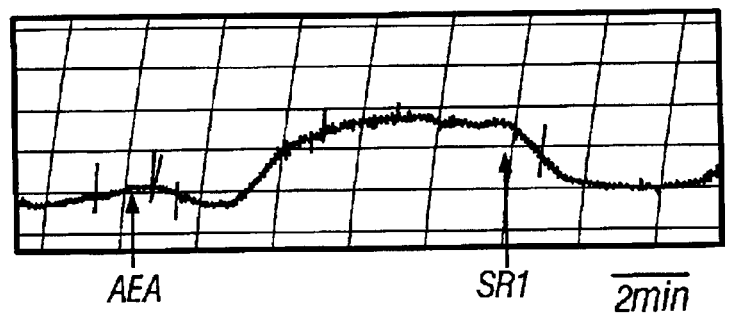
Figure 3D:
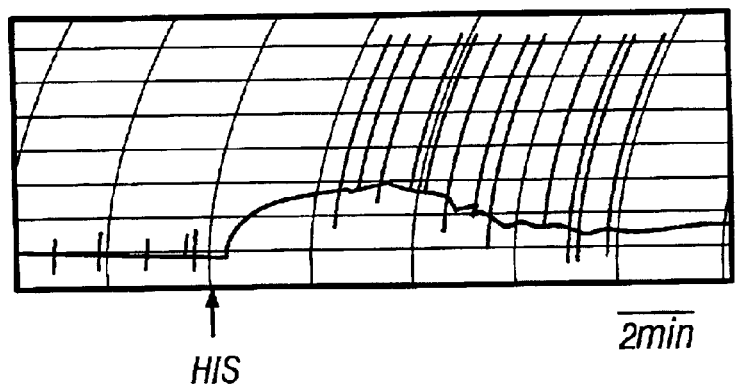
Figure 3E:
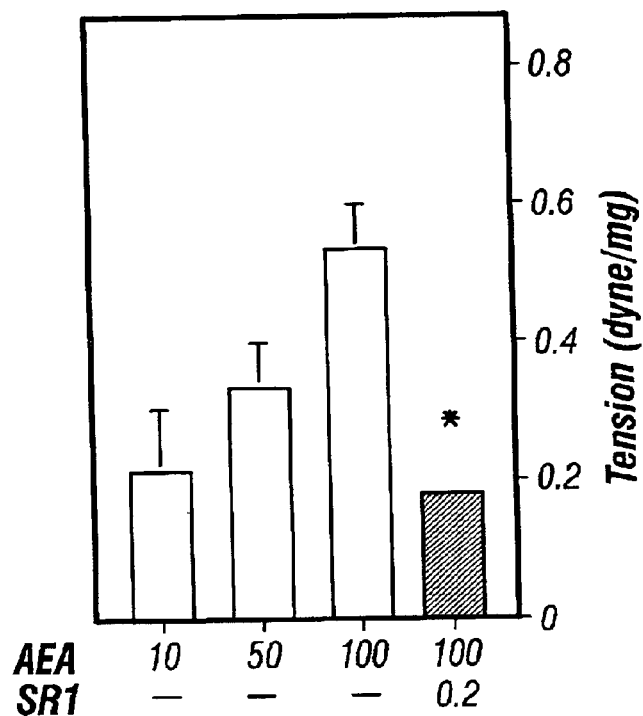

Anandamide had no direct bronchomotor action except at the highest dose tested (5 mg per kg), at which the compound elicited a small bronchoconstriction (11.8±5.9% of maximal; mean±s.e.m., n=5). To investigate further this response, the effects of anandamide in anesthetized rodents that were deprived of the bronchoconstricting tone conferred by the vagus nerve were examined. The effects are shown in FIGS. 3A–E. After vagotomy and administration of atropine (a cholinergic antagonist), which eliminate vagal influences, systemic application of anandamide produced a dose-dependent bronchoconstriction in guinea pigs and rats (i.v.; 1 mg per kg, 0±0% of maximal bronchospasm; 3 mg per kg, 12±1.7%; 5 mg per kg, 18.3±1.2%; n=3) in the presence and absence of SR141716A, as shown in FIG. 3A. Similar effects were observed when anandamide was injected into the guinea pig bronchi via a tracheal catheter (FIG. 3B), or applied to isolated strips of guinea pig lung parenchyma (FIGS. 3C–E). FIG. 3C is a representative tracing illustrating the effect of anandamide on muscle tension in guinea pig parenchyma strips and its reversal by the CB1 antagonist SR141716A. FIG. 3D is a representative tracing of the same lung strip of FIG. 3C responding to histamine. FIG. 3E shows the contractions of lung parenchyma by anandamide and antagonism by SR141716A. The slow onset of the anandamide response in guinea pig lung strips is consistent with results obtained in other isolated tissues, for example, as described in Devane, W. et al., (1992) *Science* 258, 1946–1949, while the low potency of anandamide in this preparation may be accounted for by limited tissue penetration and/or rapid inactivation.

In agreement with this possibility, the anandamide transport inhibitor N-(4-hydroxyphenyl)-arachidonamide enhanced anandamide-evoked contractions in guinea pig isolated lung strips (anandamide, 50 μM, 0.336±0.07 dyne/mg of tissue; anandamide plus N-(4-hydroxyphenyl)-arachidonamide, 28 μM, 0.638±0.06 dyne/mg of tissue; P<0.05, n=6). The CB1 antagonist SR141716A blocked anandamide bronchoconstriction in vivo and in vitro (FIGS. 3A–E), whereas the CB2 antagonist SR144528 had no such effect. The cannabinoid agonist HU210 was also potent at eliciting guinea pig bronchial muscle constriction after tracheal administration (0.1 mg per animal, 10.0±0.6% of maximal bronchospasm; 1 mg per animal, 30±1.2%; 10 mg per animal, 60±2.2%; 30 mg per animal, 100%; n=6).

Anandamide has been claimed to activate vanilloid receptors. However, the vanilloid antagonist capsazepine had no effect on anandamide-evoked bronchospasm at a dose that completely prevented the capsaicin response (0.2 mg per kg, i.v.). These results indicate that removing the vagal excitatory tone unmasked a bronchoconstricting activity of anandamide mediated through CB1 cannabinoid receptors.

Figure 4A:
FIGS. 4A–G show localization of CB1 cannabinoid receptors on axon terminals and preterminal segments in rat lungs.
Figure 4B:
Figure 4C:
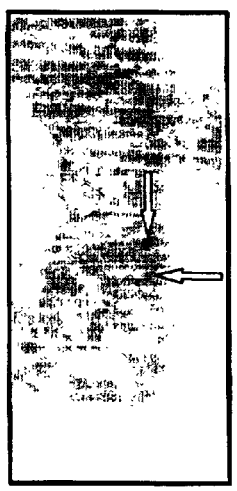
Figure 4D:
Figure 4E:
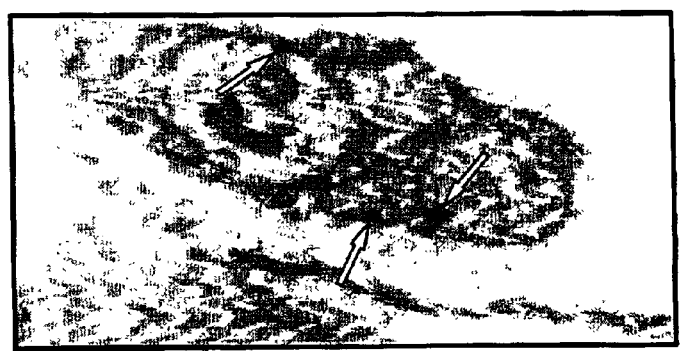

The ability of anandamide to influence bronchial muscle contractility after local administration suggests that this compound may exert its effects by activating CB1 cannabinoid receptors located within the airways. To test this possibility, the ultrastructural localization of CB1 cannabinoid receptors in rat lungs by electron microscopy, were examined using an antibody directed against the intracellular C-terminus of the rat CB1 cannabinoid receptor protein. Immunogold staining revealed that cannabinoid receptors are present on nerve fibers distributed amongst bronchial and bronchiolar smooth muscle cells, as shown in FIGS. 4A–C, or between the longitudinal and circular smooth muscle layers, where several axons were packed together into glial capsules (FIGS. 4D–E). All bundles contained at least one CB1 cannabinoid receptor-positive axon.

Detailed evaluation (20 bundles consisting of 91 axons followed through at least 25 consecutive sections) revealed that 36% of the axons were labeled with the cannabinoid receptor antibody. The gold particles labeling cannabinoid receptors were attached to the inner surface of the axon plasma membrane, either at the release site or in the preterminal segments. This is consistent with the fact that our antibody recognizes the intracellular C-terminus of the CB1 cannabinoid receptor protein. Axon terminals bearing cannabinoid receptor immunoreactivity were in close proximity to smooth muscle cells (0.2–0.5 mm) and contained a large number of small agranular vesicles along with few dense-core vesicles (FIGS. 4A–B). In some cases, cannabinoid receptor immunoreactivity was adjacent to clusters of vesicles accumulated at the plasma membrane, which most likely represent neurotransmitter release sites (FIG. 4C).

Figure 4F:
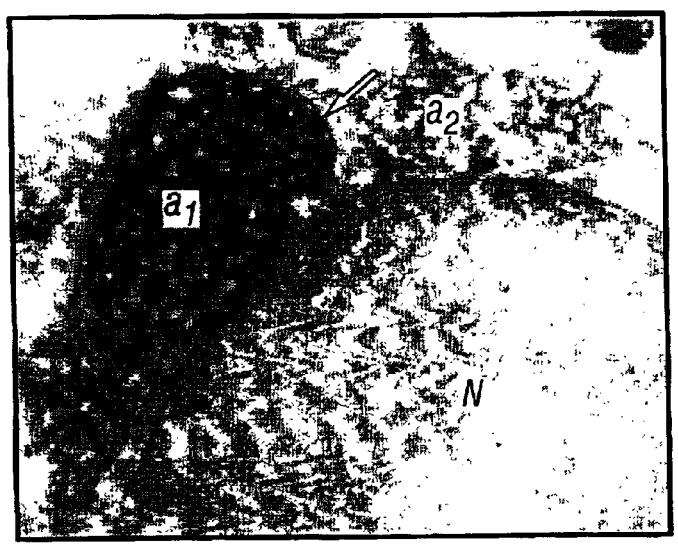
Figure 4G:
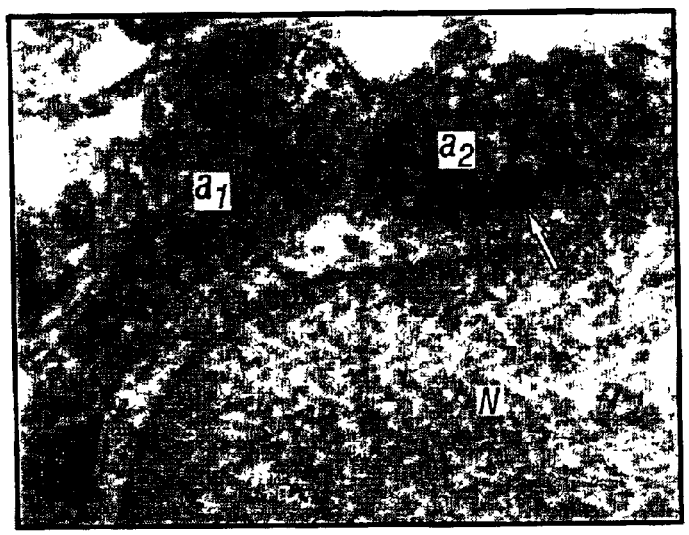

In determining whether CB1 cannabinoid receptors are localized on noradrenergic and/or non-noradrenergic fibers, a combination of immunogold staining for CB1 cannabinoid receptors and immunoperoxidase staining for neuropeptide Y (NPY), a cotransmitter in sympathetic neurons, were used. We found that 63% of NPY-bearing axons were also CB1 receptor-positive (FIGS. 4F–G). Importantly, however, extensive labeling was observed on many NPY-negative axons, suggesting that both noradrenergic and/or non-noradrenergic nerves may express cannabinoid receptors.

The finding that cannabinoid receptors are found predominantly, if not exclusively, on axon terminals of airway nerves, suggests that anandamide regulates cough and bronchial smooth muscle tone through a prejunctional mechanism. Indeed, inhibition of excitatory neurotransmission in the airways may provide a parsimonious explanation for the ability of anandamide to oppose capsaicin-evoked cough and bronchospasm. This interpretation is further supported by the ability of anandamide and other cannabinoid agonists to inhibit neurotransmitter release in peripheral tissues and in the central nervous system. The mechanism underlying the constricting actions of anandamide in animals lacking cholinergic control is currently unknown. One possibility, which is consistent with the co-localization of CB1 cannabinoid receptors with NPY, is that anandamide inhibits the release of bronchodilating mediator(s). Alternatively, anandamide may interact with cannabinoid receptors on smooth muscle. The failure to detect CB1 cannabinoid receptor immunoreactivity in lung smooth muscle may have been caused by insufficient sensitivity of the technique used or by the presence in smooth muscle of a receptor variant that is not recognized by the antibody used. Interestingly, Northern blot analyses suggest that alveolar type II cells in the lung may express two different CB1 cannabinoid receptor mRNA species.

Figure 5B:
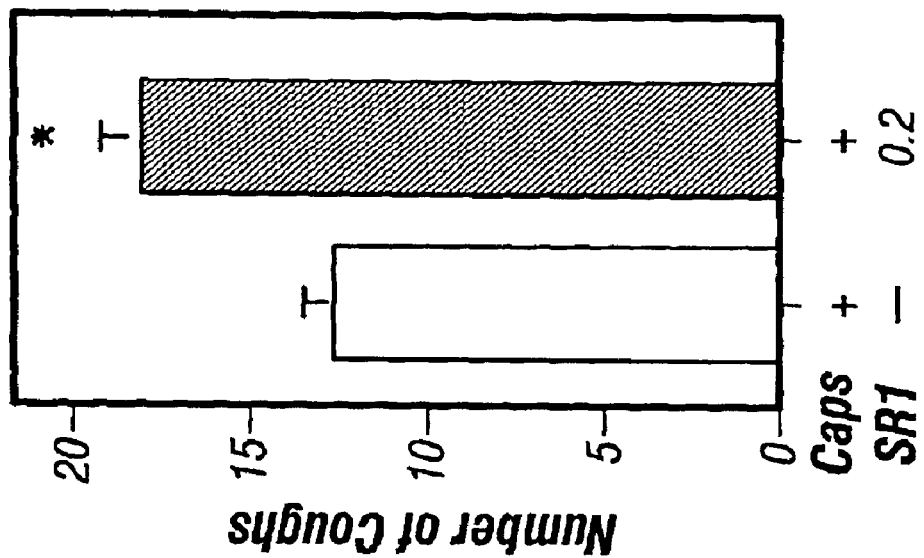
FIGS. 5A–B depict bar graphs showing the intrinsic effects of the CB1 antagonist SR141716A on capsaicin-evoked bronchospasm and cough. Results are expressed as mean±s.e.m, with n=6 for each condition. Asterisk indicates P<0.05.
Figure 5A:
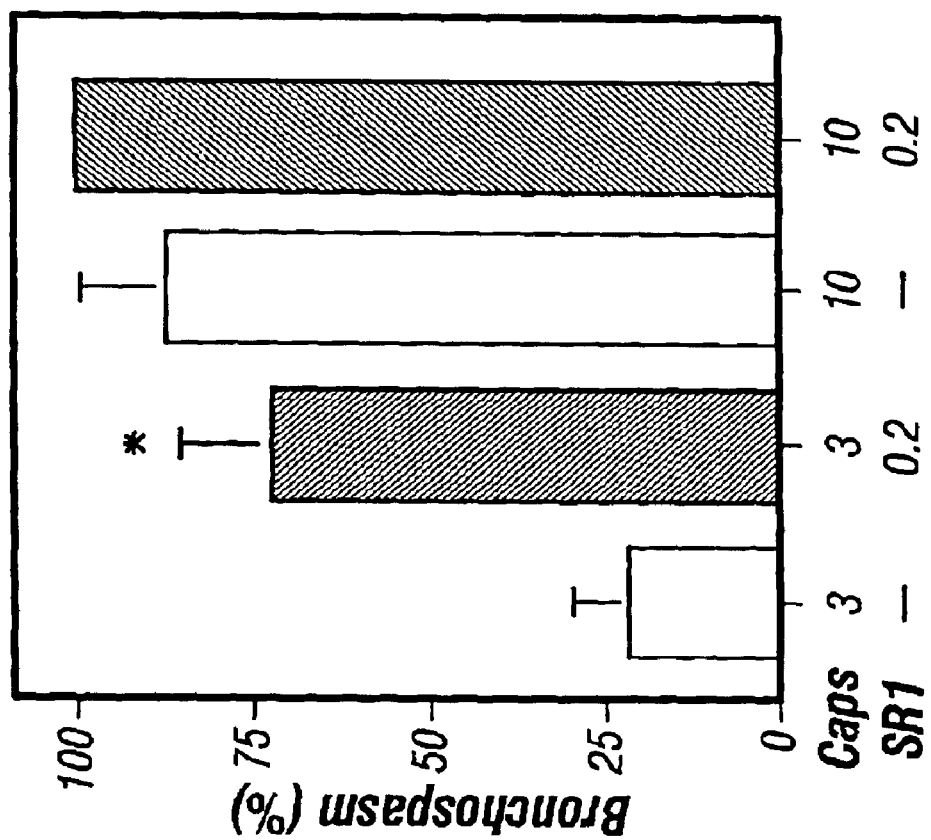
Figure 6A:
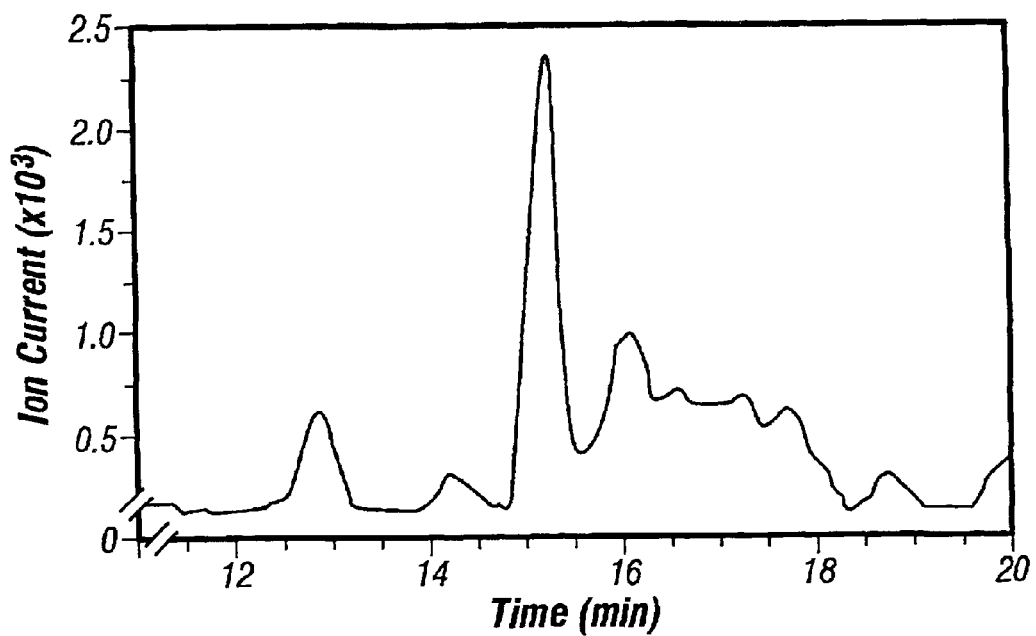
FIGS. 6A–C depict the $Ca^{2+}$-dependent biosynthesis of anandamide in rat lung tissue.
Figure 6B:
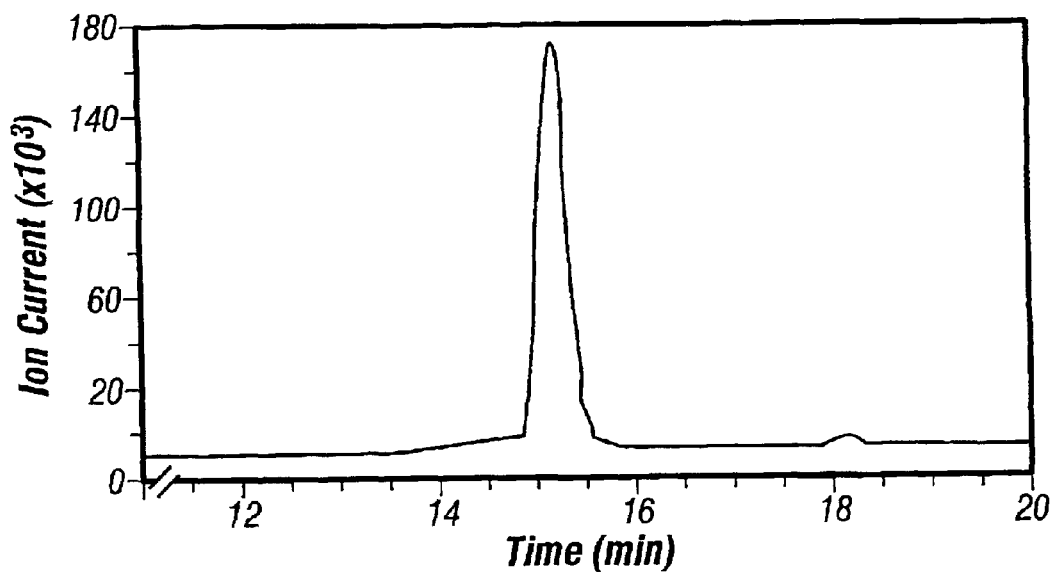
Figure 6C:
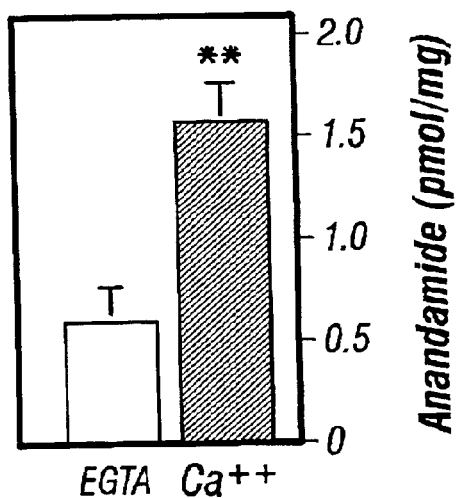

To test for the possibility that endogenous cannabinoids regulate airway responsiveness, the intrinsic effects of CB1 and CB2 antagonists on bronchospasm and cough in guinea pigs were determined. Blockade of CB1 cannabinoid receptors with SR141716A had no bronchomotor consequences per se, but significantly enhanced the bronchoconstriction and coughing evoked by capsaicin administered either via a tracheal catheter (FIGS. 5A–B) or by i.v. injection (30 mg per kg; capsaicin alone, 55.3±8.2% of maximal bronchospasm; capsaicin after SR141716A [0.5 mg per kg, i.v.], 92.3±3.4%; $P<0.05$, n=3). The CB2 antagonist SR144528 had no such effects. Although the bronchomotor actions of the CB1 antagonist may be accounted for by its inverse agonist properties, two lines of evidence suggest that this drug acted by opposing an ongoing cannabinoid modulation. First, the lack of effect seen with the CB1 antagonist in the absence of capsaicin is incompatible with an inverse agonist behavior. Second, analyses by high-performance liquid chromatography (HPLC) coupled to positive-ionization electrospray mass spectrometry (MS) revealed that anandamide is synthesized in rat lung tissue through a $Ca^{2+}$ ion-activated mechanism (FIGS. 6A–B). Rat lung membranes produced on average 0.6±0.2 pmol of anandamide per mg of protein in the presence of the $Ca^{2+}$ chelator, EGTA (1 mM); and 1.6±0.2 pmol of anandamide per mg of protein in the presence of $Ca^{2+}$ (3 mM) (mean+s.e.m., n=4; $P<0.05$ between EGTA and $Ca^{2+}$; Student's t test) (FIG. 6C). Guinea pig lung membranes produced 0.9±0.3 pmol of anandamide per mg of protein in the presence of EGTA; and 8.8±1.2 pmol of anandamide per mg of protein in the presence of $Ca^{2+}$ (n=4; $P<0.0001$; Student's t test).

Figure 7A:
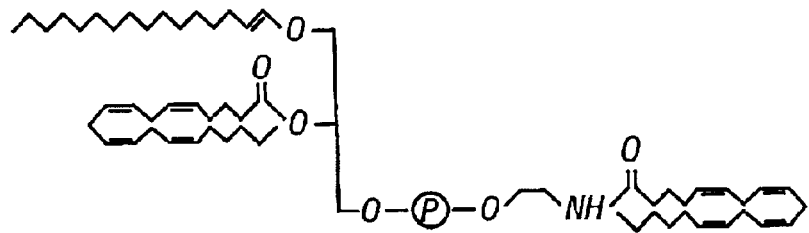
FIGS. 7A–F depicts the structure and $Ca^{2+}$ dependent biosynthesis of anandamide precursors in rat lung tissue.
Figure 7B:
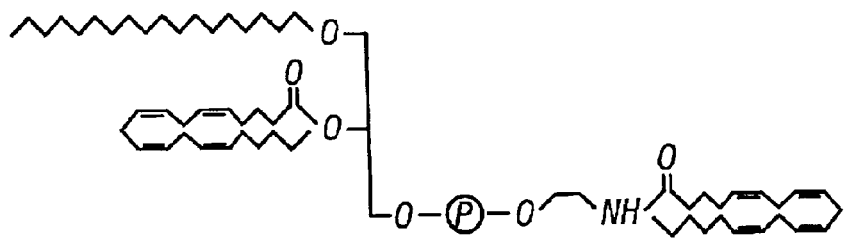
Figure 7C:
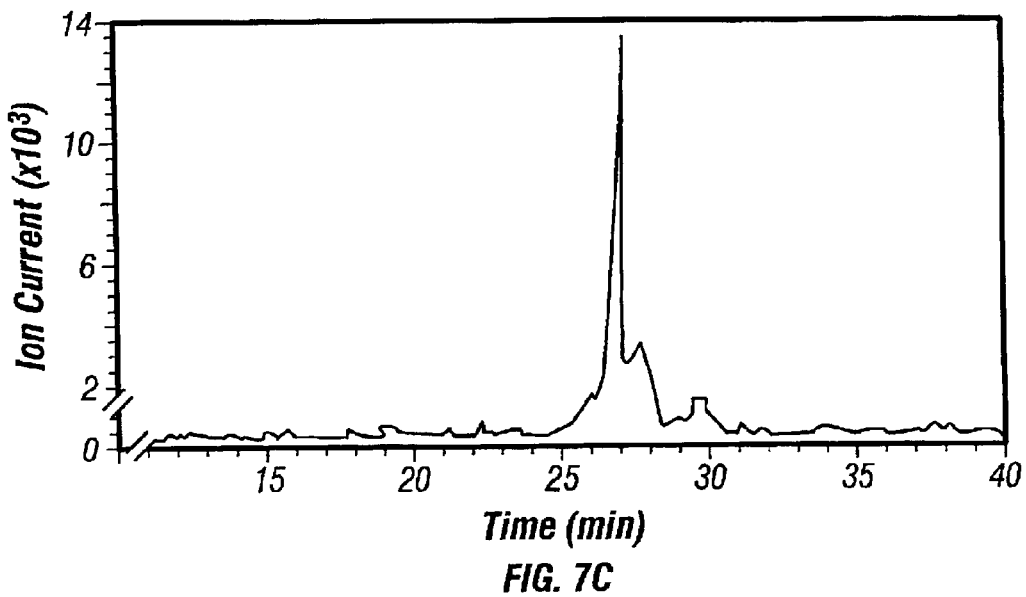
Figure 7D:
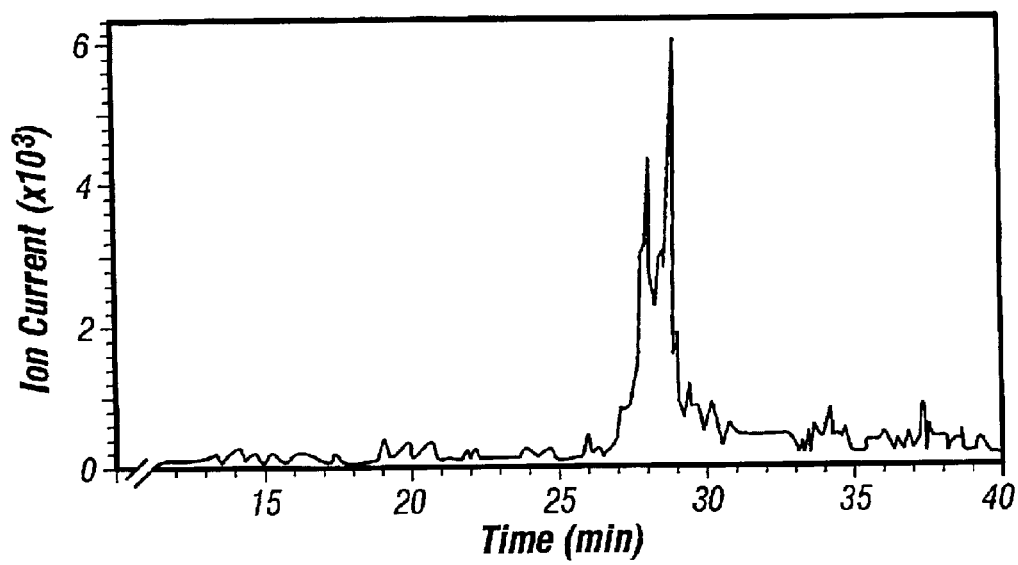
Figure 7E:
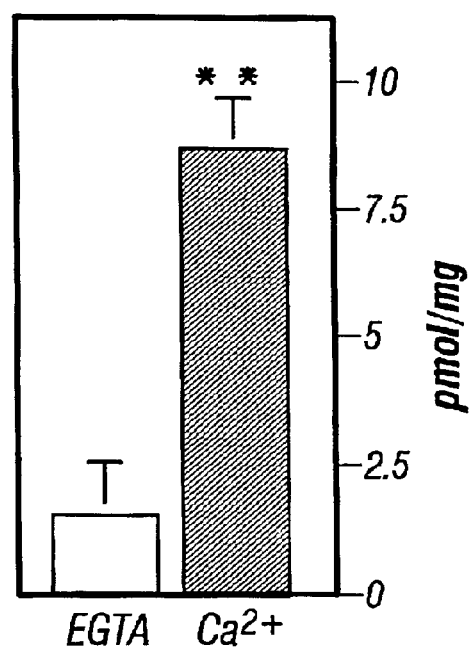
Figure 7F:
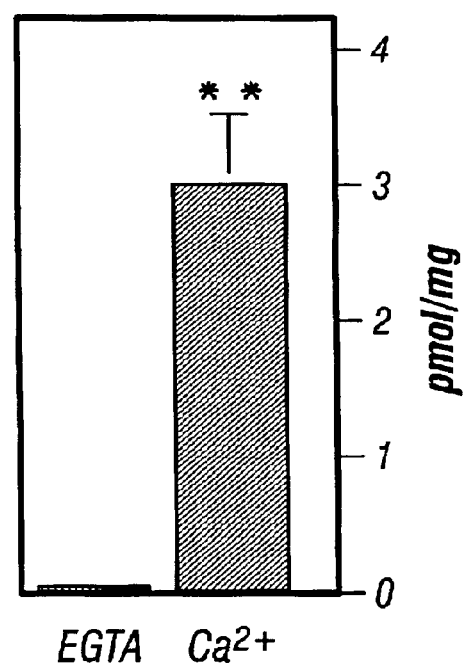

Anandamide is thought to originate from the enzymatic cleavage of N-arachidonyl phosphatidylethanolamine (NAPE), the biosynthesis of which is catalyzed by a $Ca^{2+}$-dependent N-acyltransferase activity as described in Di Marzo, V. et al. (1994) *Nature*, 372, 686–691; Sugiura, T. et al. (1996) *Eur. J. Biochem.*, 240, 53–62; Cadas, H. et al. (1997) *J. Neurosci.*, 17, 1226–1242. Using negative ionization electrospray HPLC/MS, two molecular species of NAPE in lipid extracts of rat lung membranes: alk-1-palmitoenyl-2-arachidonyl-sn-glycero-phosphoethanolamine-N-arachidonyl (NAPE 1), depicted in FIG. 7A, and alk-1-stearyl-2-arachidonyl-sn-glycero-phosphoethanolamine-N-arachidonyl (NAPE 2), depicted in FIG. 7B were identified. Identifications were based (1) on the occurrence of deprotonated molecules of appropriate mass (NAPE 1: mass-to-charge ratio (m/z) 1009; and NAPE 2, m/z 1039); and (2) on the chromatographic behavior of these components, which was similar to that of synthetic NAPE (FIGS. 7C–D). NAPE 1 and NAPE 2 were synthesized by rat lung membranes in a $Ca^{2+}$-dependent manner. The membranes produced 1.5±0.02 pmol of NAPE 1 and undetectable levels in NAPE 2 when incubated with EGTA (1 mM); and 4.4±0.5 pmol of NAPE 1 and 3.1±0.6 pmol of NAPE 2 when incubated with $Ca^{2+}$ (3 mM) (n=4; $P<0.05$ between EGTA and $Ca^{2+}$) (FIGS. 7E–F). Guinea pig lung membranes also produced NAPE 1 and NAPE 2 in a $Ca^{2+}$-dependent manner. The presence in rodent lungs of a $Ca^{2+}$-activated mechanism for the biosynthesis of anandamide and its phospholipid precursor supports a role for this endogenous cannabinoid in airway modulation. This suggests in turn that inhibitors of anandamide inactivation (compounds of formulae IV and IV) may also produce cough inhibition and bronchodilation by means of their ability to cause accumulation of anandamide at its sites of action.

These results demonstrate that activation of CB1 cannabinoid receptors by locally released cannabinoid compounds, such as anandamide, participates in the control of cough and bronchial contractility. How cannabinoids exert their control on bronchial contractility may depend, however, on the state of the bronchial muscle. When the muscle is contracted, as during capsaicin-evoked bronchospasm, anandamide may counteract this contraction, possibly by inhibiting the prejunctional release of excitatory neurotransmitters and neuropeptides. In contrast, when the smooth muscle is relaxed, as seen after removal of the constricting influence of the vagus nerve, anandamides may cause bronchoconstriction.

In summary, the present results suggest that local applications of cannabinoid agents in the airways of animals whose vagal tone is not compromised, result in cough inhibition. These effects are mediated by activation of CB1 cannabinoid receptors located on peripheral terminals of airway nerves. Furthermore, the results suggest that local or systemic administration of inhibitors of endogenous cannabinoid inactivation may also result in cough inhibition. Since the animal models used in the present experiments are predictive of anti-tussive actions/treatments in humans, it is anticipated that comparable cough-suppressing effects will be produced in human patients affected by pathological tussigenic conditions. These conditions include, but are not limited to, persistent dry cough, cancer-induced cough, and angiotensin-converting enzyme (ACE) inhibitor-induced cough.

The present invention discloses a method for treating cough in a mammal through application of at least one direct or indirect cannabinoid receptor agonist that is active at relieving or preventing cough by a peripheral action in the upper airways. The method comprises the step of administering to the mammal a cough-alleviating or cough-preventing amount of a pharmaceutical formulation comprising at least one compound having the general formulae I, II, III, IV, or IV described below.

Formula I:

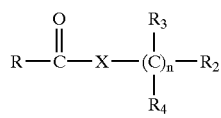

wherein X is N—R1 or O;
R is a saturated or unsaturated, chiral or achiral, cyclic or acyclic, substituted or unsubstituted hydrocarbyl group with 11 to 29 carbon atoms, optionally incorporating up to 6 oxygen or sulfur atoms;
R1, R3 and R4 are selected independently from hydrogen, alkyl (C1–4), alkenyl (C2–4), alkynyl (C2–4), cycloalkyl (C3–6), or hydroxyalkyl group with from 2 to 4 carbon atoms;
R2 is OH or O—CO-alkyl, where the alkyl group has from 1 to 4 carbon atoms; and
n is selected from 2 to 4.
When R2 is OH and X is N—H, they may be combined through the carbonyl group to form a heterocyclic ring structure, e.g. an oxazolidinone ring. Alternatively, when R2 is OH and X is N—H, they may be combined to form a heterocyclic ring structure, e.g a morpholine ring.

Formula II:

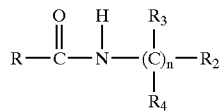

wherein R is a saturated or unsaturated, substituted or unsubstituted hydrocarbyl group with from 15 to 29 carbon atoms, optionally incorporating up to 3 oxygen or sulfur atoms;
R3 and R4 are selected independently from hydrogen, alkyl (C1–4), alkenyl (C2–4), alkynyl (C2–4), cycloalkyl (C3–6), or hydroxyalkyl group with from 2 to 4 carbon atoms;
R2 is OH or O—CO-alkyl, where the alkyl group has from 1 to 4 carbon atoms; and
n is selected from 2 to 4.
When R2 is OH and X is N—H, they may be combined to form a heterocyclic ring structure.

Formula III:

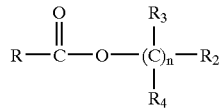

wherein R is a saturated or unsaturated, substituted or unsubstituted hydrocarbyl group with from 15 to 29 carbon atoms, optionally incorporating up to 3 oxygen atoms;
R3 and R4 are selected independently from hydrogen, alkyl (C1–4), alkenyl (C2–4), alkynyl (C2–4), cycloalkyl (C3–6), or hydroxyalkyl group with from 2 to 4 carbon atoms;

R2 is OH or O—CO-alkyl, where the alkyl group has from 1 to 4 carbon atoms; and
n is selected from 2 to 4.

Formula IV:

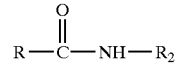

wherein R is a polyunsaturated, substituted or unsubstituted hydrocarbyl group with from 18 to 22 carbon atoms;
R2 is selected independently from substituted or unsubstituted cycloalkyl (C3–6) group and substituted or unsubstituted phenyl group (e.g., p-hydroxyphenyl, p-hydroxy-o-methyl-phenyl).

Formula V:

wherein R1 is a saturated or polyunsaturated, substituted or unsubstituted hydrocarbyl group with from 6 to 22 carbon atoms;
X is —C=O or $SO_2$—; and
R2 is a halogen or a halogen-substituted methyl group.

Pharmaceutical Formulations

The pharmaceutical compositions used in the methods of the invention can be administered by any means known in the art, e.g., parenterally, topically, orally, or by local administration, such as aerosol or transdermally. The pharmaceutical compositions can be formulated in any way and can be administered in a variety of unit dosage forms depending upon the condition, disease, degree, or cause of the cough, the general medical condition of the patient, the resulting preferred method of administration and the like. Routine means to determine drug regimens, formulations, and administration to practice the methods of the invention are well described in the patent and scientific literature, see, e.g., the latest edition of *Remington's Pharmaceutical Sciences*, Maack Publishing Co, Easton Pa.

Pharmaceutical formulations can be prepared according to any method known to the art for the manufacture of pharmaceuticals. The pharmacological composition of the invention can comprise other active agents such as anti-inflammatory compounds. Pharmaceutically acceptable compounds can contain a physiologically acceptable compound that acts to stabilize the composition or to increase or decrease the absorption of the agent and/or pharmaceutical composition. A formulation can be admixtured with non-toxic pharmaceutically acceptable excipients that are suitable for manufacture.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be obtained through combination of cannabinoids of the invention with a solid excipient, optionally grinding a resulting mixture, and processing the mixture of granules, after adding suitable additional compounds, if desired, to obtain tablets or dragee cores. Suitable solid excipients such as carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth;

and proteins, e.g., gelatin and collagen. Disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, e.g., push-fit capsules made of gelatin, as well as soft, sealed capsules made of gelatin and a coating such as glycerol or sorbitol. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., N-(4-hydroxyphenyl) arachidonamide) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil-based pharmaceuticals are particularly useful for administration of hydrophobic active agents. Oil-based suspensions can be formulated by suspending an active agent (e.g., N-(4-hydroxyphenyl) arachidonamide) in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) *J. Pharmacol. Exp. Ther.* 281:93–102.

The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Dispersible powders and granules suitable for preparation of an aqueous suspension by the addition of water can be formulated in admixture with a dispersing, suspending and/or wetting agent, and one or more preservatives. Suitable dispersing or wetting agents and suspending agents are exemplified by those disclosed above. Additional excipients, e.g., sweetening, flavoring and coloring agents, can also be present.

In the methods of the invention, the pharmaceutical compounds can also be administered by intranasal or intrabronchial routes including insufflation, powders, and aerosol formulations (for examples of steroid inhalants, see Rohatagi (1995) *J. Clin. Pharmacol.* 35:1187–1193; Tjwa (1995) *Ann. Allergy Asthma Immunol.* 75:107–111). For example, aerosol formulations can be placed into pressurized acceptable propellants, such as dichlorodifluoromethane, propane, nitrogen, and the like. They also may be formulated as pharmaceuticals for non-pressured preparations such as in a nebulizer or an atomizer. Typically, such administration is in an aqueous pharmacologically acceptable buffer.

In the methods of the invention, the pharmaceutical compounds can be delivered transdermally, by a topical route, formulated as applicator sticks, solutions, suspensions, emulsions, gels, creams, ointments, pastes, jellies, paints, powders, and aerosols.

In the methods of the invention, the pharmaceutical compounds can also be delivered as microspheres for slow release in the body. For example, microspheres can be administered via intradermal injection of the drug, which is slowly released subcutaneously; see Rao (1995) *J. Biomater. Sci. Polym. Ed.* 7:623–645; as biodegradable and injectable gel formulations, see, e.g., Gao (1995) *Pharm. Res.* 12:857–863 (1995); or, as microspheres for oral administration, see, e.g., Eyles (1997) *J. Pharm. Pharmacol.* 49:669–674. Both transdermal and intradermal routes afford constant delivery for weeks or months.

In the methods of the invention, the pharmaceutical compounds can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM to 50 mM histidine, 0.1% to 2% sucrose, 2% to 7% mannitol at a pH range of 4.5 to 5.5, that is combined with buffer prior to use.

In the methods of the invention, the pharmaceutical compounds can be parenterally administered, such as by intravenous (IV) administration. These formulations will commonly comprise a solution of active agent dissolved in a pharmaceutically acceptable carrier. Acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well-known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol.

In another embodiment, the formulations of the invention can be delivered by the use of liposomes which fuse with the cellular membrane or are endocytosed, e.g., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) *J. Microencapsul.* 13:293–306; Chonn (1995) *Curr. Opin. Biotechnol.* 6:698–708; Ostro (1989) *Am. J. Hosp. Pharm.* 46:1576–1587.

In the methods of the invention, a pharmaceutical composition is administered in an amount sufficient to ameliorate cough. The amount of pharmaceutical composition adequate to accomplish this is defined as a "therapeutically effective dose." The dosage schedule and amounts effective for this use, i.e., the "dosing regimen," will depend upon a variety of factors, including the stage and/or severity of the disease, condition, or other cause of the cough, the severity of the cough, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) *J. Steroid Biochem. Mol. Biol.* 58:611–617; Groning (1996) *Pharmazie* 51:337–341; Fotherby (1996) *Contraception* 54:59–69; Johnson (1995) *J. Pharm. Sci.* 84:1144–1146; Rohatagi (1995) *Pharmazie* 50:610–613; Brophy (1983) *Eur. J. Clin. Pharmacol.* 24:103–108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, e.g., dose schedule and dosage levels of any CB1 cannabinoid receptor activator administered practicing the methods of the invention.

Single or multiple administrations of formulations can be given depending on the dosage and frequency as required and tolerated by the patient. The formulations should provide a sufficient quantity of active agent to effectively treat the cough. In one example, the concentration of cannabinoid compounds, such as anandamide, in the pharmaceutically acceptable excipient is between about 0.1–100 mg per dose in an aqueous solution. As another example, one typical pharmaceutical formulations for oral administration of N-(4-hydroxyphenyl) arachidonamide is in a daily amount of between about 0.5 to about 20 mg per kilogram of body weight per day. In an alternative embodiment, dosages are from about 1 mg to about 4 mg per kg of body weight per patient per day are used. Lower dosages can be used, particularly when the drug is administered to an anatomically secluded site, such as the lung space, in contrast to administration systemically into the blood stream. Substantially higher dosages can be used in topical administration. Actual methods for preparing parenterally administrable formulations will be known or apparent to those skilled in the art and are described in more detail in such publications as Remington's, supra. See also Nieman, In "Receptor Mediated Antisteroid Action," Agarwal, et al. (1987) eds., De Gruyter, New York.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Chemical Synthesis

Anandamide and other fatty acid ethanolamides can be synthesized following standard procedures described in Giuffrida, A. et al. (1998) *FEBS Lett.*, 422, 373–376. The synthesis of 2-arachidonyleglycerol and other monoacylglycerides can be accomplished as described in B. Serdarevich, (1967) *Journal of the Oil Chemist Society*, 44, 381–393. The drugs were dissolved in dimethylsulphoxide (DMSO), and administered in physiological saline containing 10% DMSO.

EXAMPLE 2

Biological Assays

Bronchospasm.

Dunkin-Hartley guinea pigs (Charles-River, weighing 200–400 g) or Wistar rats (Charles-River, weighing 200–300 g) were anesthetized with pentobarbital (40 mg per k.g., intraperitoneal) and fentanyl (25 mg per kg, intramuscular). The trachea and carotid artery were catheterized to measure airway obstruction and systemic blood pressure. The jugular vein was catheterized to administer drugs. Pancuronium bromide (4 mg per kg, intravenous) was administered to prevent spontaneous breathing. The animals were ventilated with room air using a rodent ventilator (U. Basile, Comerio, Italy) run at 60 strokes per min; stroke volume was 3–7 ml. Airway resistance was measured by using a differential pressure transducer (U. Basile) connected by the side-arm of the tracheal catheter to a bronchospasm transducer. Bronchospasm was expressed as a percent of the maximal response, which was determined by clamping the tracheal catheter before and after each experiment. Drugs were dissolved in saline containing 10% dimethylsulphoxide, and injected via the jugular vein. Responses were evaluated at their peak. Arterial blood pressure was measured continuously with a pressure transducer connected to a recorder (U. Basile). To abolish vagal influences on bronchial musculature, in some experiments the vagus nerves were bilaterally transected and administered with atropine sulfate (2 mg per kg, i.v.).

Cough.

Conscious guinea pigs were individually exposed for 4 min to aerosolized capsaicin (0.3 mM) while recording coughs by using a microphone placed in the exposure chamber as described in Bolser, D. C., et al (1995)(*Eur. J. Pharmacol.*, 276, R1–R3. Each animal was treated only once with capsaicin. Aerosols were prepared with an Air Lister Basic apparatus (Hatu, Italy), regulated at an emission flow rate of 6 liters per min.

Isolated Lung Strips.

Guinea pig parenchimal strips were prepared essentially as described in Samhoun, M. N., et al. (1984) *Prostaglandins*, 27, 711–724. The strips were placed in 10-ml organ baths containing Krebs' buffer (in mM: NaCl, 118; KCl, 4; K2HPO4, 1.2; MgSO4, 1.2; CaCl2, 2.5; NaHCO3, 25.0; glucose, 11.2; supplemented with 7 mM atropine sulfate and 15 mM indomethacin) at 37° C. and aerated with an oxygen/carbon dioxide mixture (95/5%). Muscle contractions were recorded with an isometric force transducer (U. Basile) and expressed in dyne per mg of fresh tissue.

EXAMPLE 3

Electron Microscopy

The lungs were removed from 3 rats perfused with a phosphate-buffered (PB, 0.1 M) fixative containing 4% paraformaldehyde, 0.2% picric acid and 0.05% glutaraldehyde, and were further fixed for 24 h. Immunohistochemical analyses were conducted as described in Katona, I. et al. (1999) *J. Neurosci.*, 19, 4544–4558. Rabbit C-terminal anti-CB1 and anti-NPY antibodies were used at 1:5000 and 1:20,000 dilution, respectively. The specificity of the NPY antibody was reported previously in Csiffary, A., et al. (1990) *Brain Res.* 506, 215–222.

EXAMPLE 4

Membrane Preparation and Lipid Extraction

Lung particulate fractions were prepared as described in Désarnaud, F., et al. (1995) *J. Biol. Chem.*, 270, 6030–6035. Incubations were performed for 1 h at 37° C. in Tris buffer (50 mM, pH 7.4) containing $CaCl_2$ (3 mM) or EGTA (1 mM) and 2 mg per ml of membrane protein. Reactions were stopped by adding cold methanol and the lipids were extracted with chloroform. Before HPLC/MS analysis, anandamide and NAPE were fractionated by silica gel column chromatography as described in Cadas, H., et al. (1997) *J. Neurosci.*, 17, 1226–1242.

EXAMPLE 5

High Performance Liquid Chromatography/Mass Spectrometry (HPLC/MS)

The anandamide was identified and quantified by reversed-phase HPLC coupled to positive ionization electrospray MS, by using an isotope-dilution method described in Giuffrida, A., Rodríguez de Fonseca, F., et al. (2000) *Anal. Biochem.*, 280, 87–93. NAPE species were purified by reversed-phase HPLC on a C18 Bondapak column (300×3.9 mm I.D., 5 mm) (Waters) maintained at 20° C. and interfaced with an Agilent HP1100 model mass spectrometer. HPLC conditions consisted of a linear gradient of methanol in water (from 75% to 100% methanol in 30 min) with a flow rate of 1 ml/min. Under these conditions, different NAPE species were eluted from the column as a group of peaks at retention times comprised between 27 and 29 min. MS analyses were performed with the electrospray ion source set in the negative ionization mode, the Vcap set at 5 kV, and the fragmentor voltage set at 200 V. Nitrogen was used as a drying gas at a flow rate of 12 l/min. The drying gas temperature was set at 350° C. and the nebulizer pressure at 30 PSI. For quantitative purposes, diagnostic ions (deprotonated molecular ions, $(M-H)^-$) were extracted from full scan data and quantified by comparison with an external standard (1-palmityl-2-oleyl-sn-glycero-phosphoethanolamine-N-arachidonyl, Avanti Polar Lipids).

EXAMPLE 6

Data Analysis

Results are expressed as means±s.e.m. The significance of differences among groups was evaluated using Student's t test or analysis of variance followed by Dunnett's test.

All publications, Genebank references, patents, patent applications cited herein are hereby expressly incorporated by reference for all purposes. A number of embodiments of the invention have been described. Nevertheless, it will be understood that various modifications may be made without departing from the spirit and scope of the invention. Accordingly, other embodiments are within the scope of the following claims.

What is claimed is:

1. A method of ameliorating cough in a subject comprising the local administration to the upper respiratory airways of the subject of a CB1 cannabinoid receptor agonist of formula I:

$$R-\overset{O}{\underset{}{\overset{\|}{C}}}-X-\overset{R_3}{\underset{R_4}{\overset{|}{\underset{|}{C}}}}_n-R_2$$

wherein X is $N-R_1$ or O;

R is a saturated or unsaturated, chiral or achiral, cyclic or acyclic, substituted or unsubstituted hydrocarbyl group, wherein the hydrocarbyl group has 11 to 29 carbon atoms;

$R_1$, $R_3$ and $R_4$ are selected independently from hydrogen, alkyl (C1–4), alkenyl (C2–4), alkynyl (C2–4), cycloalkyl (C3–6), or a hydroxyalkyl group with from 2 to 4 carbon atoms;

$R_2$ is OH or O—CO-alkyl, where the alkyl group has from 1 to 4 carbon atoms; and n is selected from 2 to 4.

2. A method of ameliorating cough comprising the local administration to the upper respiratory airways of a subject in need of such treatment of a CB1 cannabinoid receptor agonist of formula II:

$$R-\overset{O}{\underset{}{\overset{\|}{C}}}-\overset{H}{\underset{}{\overset{|}{N}}}-\overset{R_3}{\underset{R_4}{\overset{|}{\underset{|}{C}}}}_n-R_2$$

wherein R is a saturated or unsaturated, substituted or unsubstituted hydrocarbyl group with from 15 to 29 carbon atoms;

$R_3$ and $R_4$ are selected independently from hydrogen, alkyl (C1–4), alkenyl (C2–4), alkynyl (C2–4), cycloalkyl (C3–6), or a hydroxyalkyl group with from 2 to 4 carbon atoms;

$R_2$ is OH or O—CO-alkyl, where the alkyl group has from 1 to 4 carbon atoms; and n an integer is selected from 2 to 4.

3. A method of ameliorating cough comprising the local administration to the upper respiratory airways of a subject in need of such treatment of 2-arachidonylglycerol.

4. A method of ameliorating cough in a subject comprising the local administration to the upper respiratory airways of the subject or the systemic administration to the subject of an inhibitor of endogenous cannabinoid inactivation of formula IV:

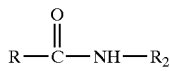

wherein R is a polyunsaturated, substituted or unsubstituted hydrocarbyl group, wherein the hydrocarbyl group has from 18 to 22 carbon atoms;

$R_2$ is selected independently from substituted or unsubstituted cycloalkyl (C3–6) group and substituted or unsubstituted phenyl group.

5. The method of claim 4, wherein the phenyl group is selected from the group consisting of p-hydroxyphenyl and p-hydroxy-o-methyl-phenyl.

6. A method of ameliorating cough comprising the local administration to the upper respiratory airways of a subject or the systemic administration to subject in need of such treatment of an inhibitor of endogenous cannabinoid inactivation of formula V:

wherein $R_1$ is a saturated or polyunsaturated, substituted or unsubstituted hydrocarbyl group, wherein the hydrocarbyl group has from 6 to 22 carbon atoms;

X is —C=O or $SO_2$—; and $R_2$ is a halogen or a halogen-substituted methyl group.

7. The method of claim 1, wherein the cough is selected from the group consisting of a persisting dry cough resulting from airway irritation and/or infection, an angiotensin converting enzyme (ACE) inhibitors-induced cough, and a cancer-induced cough.

8. The method of claim 4, wherein the method further comprises administration of a CB1 cannabinoid receptor agonist of formula I:

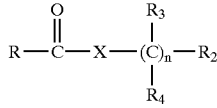

wherein X is N—$R_1$ or O;

R is a saturated or unsaturated, chiral or achiral, cyclic or acyclic, substituted or unsubstituted hydrocarbyl group, wherein the hydrocarbyl group has 11 to 29 carbon atoms;

$R_1$, $R_3$ and $R_4$ are each selected independently from hydrogen, alkyl (C1–4), alkenyl (C2–4), alkynyl (C2–4), cycloalkyl (C3–6), or a hydroxyalkyl group with from 2 to 4 carbon atoms;

$R_2$ is OH or O—CO-alkyl, where the alkyl group has from 1 to 4 carbon atoms; and n is an integer from 2 to 4.

9. The method of claim 5, wherein the method further comprises administration of a CB1 cannabinoid receptor agonist of formula I:

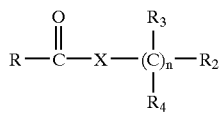

wherein X is N—$R_1$ or O;

R is a saturated or unsaturated, chiral or achiral, cyclic or acyclic, substituted or unsubstituted hydrocarbyl group, wherein the hydrocarbyl group has 11 to 29 carbon atoms;

$R_1$, $R_3$ and $R_4$ are each selected independently from hydrogen, alkyl (C1–4), alkenyl (C2–4), alkynyl (C2–4), cycloalkyl (C3–6), or a hydroxyalkyl group with from 2 to 4 carbon atoms;

$R_2$ is OH or O—CO-alkyl, where the alkyl group has from 1 to 4 carbon atoms; and n is an integer from 2 to 4.

10. A method of ameliorating cough comprising the local administration of a CB1 cannabinoid receptor agonist of formula II to the upper respiratory airways of a patient in need of such treatment and whose vagal control of airway responsiveness is functional, wherein the formula I is:

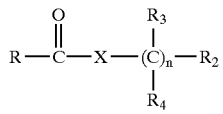

wherein X is N—$R_1$ or O;

R is a saturated or unsaturated, chiral or achiral, cyclic or acyclic, substituted or unsubstituted hydrocarbyl group, wherein the hydrocarbyl group has 11 to 29 carbon atoms;

$R_1$, $R_3$ and $R_4$ are selected independently from hydrogen, alkyl (C1–4), alkenyl (C2–4), alkynyl (C2–4), cycloalkyl (C3–6), or a hydroxyalkyl group with from 2 to 4 carbon atoms;

$R_2$ is OH or O—CO-alkyl, where the alkyl group has from 1 to 4 carbon atoms; and n is an integer from 2 to 4.

11. The method of claim 1 wherein the agonist of formula I is selected from the group consisting of arachidonylethanolamide (anandamide), (R)-(+)arachidonyl-1$^1$-hydroxy-2$^1$-propylamide, cis-7, 10,13,16-docosatetraenoylethanolamide, homo-delta-linoleyethanolamide, and N-propyl-arachidonylethanolamide.

12. The method of claim 4 wherein the cannabinoid inactivation inhibitor of formula IV is 4-(hydroxylphenyl)-arachidonylamide.

13. The method of claim 10, wherein the method further comprises local or systemic administration of a pharmaceutical composition comprising a cannabinoid inactivation inhibitor of formula IV, or formula V, or any combination thereof, wherein the formula IV is

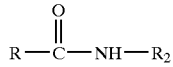

wherein R is a polyunsaturated, substituted or unsubstituted hydrocarbyl group, wherein the hydrocarbyl group has from 18 to 22 carbon atoms; $R_2$ is selected independently from substituted or unsubstituted cycloalkyl (C3–6) group and substituted or unsubstituted phenyl group;
and the formula V is

wherein $R_1$ is a saturated or polyunsaturated, substituted or unsubstituted hydrocarbyl group, wherein the hydrocarbyl group has from 6 to 22 carbon atoms;

X is —C=O or $SO_2$—; and $R_2$ is a halogen or a halogen-substituted methyl group.

14. The method of claim 10 wherein the pharmaceutical composition is formulated for local delivery.

15. The method of claim 14 wherein the local delivery is by aerosol.

16. The method of claim 13 wherein the pharmaceutical composition is formulated for local delivery.

17. The method of claim 16 wherein the local delivery is by aerosol.

18. The method of claim 13 wherein the pharmaceutical composition is formulated for systemic delivery.

19. The method of claim 18 wherein the systemic delivery is by oral administration or intravenous administration.

20. A pharmaceutical composition comprising a locally acting cannabinoid of formulae I, wherein the cannabinoid ameliorates cough and produces, at most, clinically insignificant dysphoric side effects, and wherein formula I is:

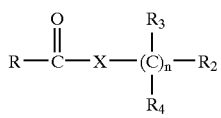

wherein X is N—$R_1$ or O;

R is a saturated or unsaturated, chiral or achiral, cyclic or acyclic, substituted or unsubstituted hydrocarbyl group, wherein the hydrocarbyl group has 11 to 29 carbon atoms;

$R_1$, $R_3$ and $R_4$ are selected independently from hydrogen, alkyl (C1–4), alkenyl (C2–4), alkynyl (C2–4), cycloalkyl (C3–6), or a hydroxyalkyl group with from 2 to 4 carbon atoms;

$R_2$ is OH or O—CO-alkyl, where the alkyl group has from 1 to 4 carbon atoms; and n is an integer from 2 to 4;

and wherein the cannabinoid is formulated as an aerosol or insufflation powder, or is nebulized.

21. The pharmaceutical composition of claim 20 further comprising a pharmaceutically acceptable excipient.

22. A method of ameliorating cough in a subject comprising the local administration to the upper respiratory airways of the subject of a CB1 cannabinoid receptor agonist of formula I:

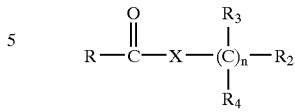

where R is a saturated or unsaturated, chiral or achiral, cyclic or acyclic, substituted or unsubstituted hydrocarbyl group, wherein the hydrocarbyl group has from 11 to 29 carbon atoms;

X is NH and $R_2$ is OH $R_1$, $R_3$ and $R_4$ are selected independently from the group consisting of hydrogen, alkyl (C1–4), alkenyl (C2–4), alkynyl (C2–4), cycloalkyl (C3–6), and a hydroxyalkyl group with from 2 to 4 carbon atoms;

n is selected from 2 to 4 and wherein $R_2$ and X are joined together to form a heterocyclic ring.

23. The method of claim 22 where the heterocyclic ring is a morpholine or oxazepine ring.

24. The method of claim 1, wherein the compound has the formula:

Formula Ib

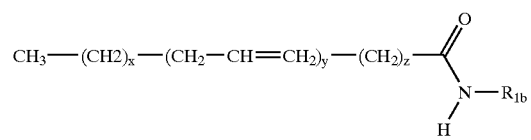

wherein $R_{1b}$ is $(CH_2)_p$—$(CH_2)_q$—$(CH_2)_r$—OH, wherein p, q and r are each an integer of from 1 to 4; provided that p+q+r are less than or equal to 4, x is an integer of from 0 to 18, y is an integer of from 0 to 8, and z is an integer of from 0 to 18.

25. The method of claim 1, wherein $R_1$ and $R_3$ are each hydrogen, and $R_2$ is hydroxy and n is 2.

26. The method of claim 1, wherein R is an acyclic and unsubstituted hydrocarbyl group.

27. The method of claim 2, wherein R is an acyclic and unsubstituted hydrocarbyl group.

28. The method of claim 1, wherein the agonist is selective for the CB1 cannabinoid receptor over the CB2 cannabinoid receptor.

* * * * *